(12) United States Patent
Kondo et al.

(10) Patent No.: US 7,812,184 B2
(45) Date of Patent: Oct. 12, 2010

(54) PRODUCTION METHOD OF OPTICALLY ACTIVE EPOXY COMPOUND, COMPLEX USED FOR THE METHOD AND PRODUCTION METHOD OF THE COMPLEX

(75) Inventors: Shoichi Kondo, Funabashi (JP); Kazuhiro Matsumoto, Fukuoka (JP); Yuji Sawada, Fukuoka (JP); Tsutomu Katsuki, Fukuoka (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 243 days.

(21) Appl. No.: 11/979,815

(22) Filed: Nov. 8, 2007

(65) Prior Publication Data
US 2008/0234502 A1 Sep. 25, 2008

(30) Foreign Application Priority Data
Mar. 23, 2007 (JP) ............................. 2007-077871

(51) Int. Cl.
*C07D 301/12* (2006.01)
(52) U.S. Cl. ..................... 549/531; 549/523; 556/56; 564/367
(58) Field of Classification Search ............... 549/531, 549/523; 556/56; 564/306, 367
See application file for complete search history.

(56) References Cited

FOREIGN PATENT DOCUMENTS

WO    WO 2006/087874 A1    8/2006

OTHER PUBLICATIONS

Matsumoto et al., Synlett, 2006, (20), 3545-3547, Aug. 12, 2006.*
Katsuki et al.; "The First Practical Method for Asymmetric Epoxidation;" *J. Am.Chem. Soc.*; 1980; pp. 5974-5976; 102; American Chemical Society.
Jacobsen et al.; "Comprehensive Asymmetric Catalysis;" 1999; pp. 649-677; vol. II; 21; Springer; Germany.
Katsuki, T. (Edited by Jon A. McCleverty, Thomas J. Meyer); "Comprehensive Coordination Chemistry II;" 2003; pp. 207-264; vol. 9; Elsevier Ltd.; Oxford, United Kingdom.
Shu et al.; "An efficient ketone-catalyzed asymmetric epoxidation using hydrogen peroxide (H2O2) as primary oxidant;" *Tetrahedron*; 2001; pp. 5213-5218; vol. 57; Elsevier Science Ltd.
Colonna et al.; "Highly enantioselective epoxidation by means of polyaminoacids in a triphase system: Influence of structural Variations within the catalysts;" *Tetrahedron*; 1983; pp. 1635-1641; vol. 39; No. 9; Pergamon Press Ltd.
Matsumoto et al.; "Construction of Pseudo-Heterochiral and Homochiral Di-μ-oxotitanium (Schiff base) Dimers and Enantioselective Epoxidation Using Aqueous Hydrogen Peroxide;" *Agnewandte Chemie Int. Ed.*; 2005; pp. 4935-4939; vol. 44; Wiley-VCH Verlag GmbH & Co. KgaA, Weinheim.
Sawada et al.; "Titanium-Salan-Catalyzed Asymmetric Epoxidation with Aqueous Hydrogen Peroxide as the Oxidant;" *Agnewandte Chemie Int. Ed.*; 2006; pp. 3478-3480; vol. 45; Wiley-VCH Verlag GmbH & Co. KgaA, Weinheim.

* cited by examiner

*Primary Examiner*—Janet L Andres
*Assistant Examiner*—David E Gallis
(74) *Attorney, Agent, or Firm*—Oliff & Berridge, PLC

(57) ABSTRACT

[Problem] To provide a production method of optically active epoxy compound, and a complex used for the production method and a production method of the complex.

[Means for solving the problem] The skeleton that is necessary for expressing a high catalyst activity of optically active titanium salan complex of formulae (1) and (1')

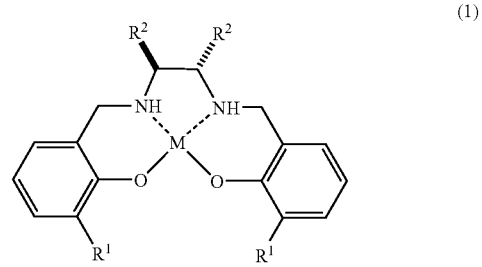

(1)

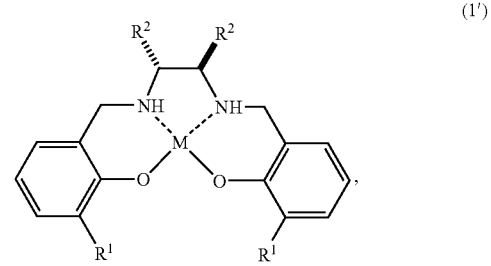

(1')

and the substituent that is useful therefor and the position of the substituent are identified, and it is found that optically active epoxy compounds can be produced with a high enantioselectivity and a high chemical yield compared with a case where the prior optically active titanium salan complex is used. The production method comprises subjecting a prochiral compound (formula (4), (5) or (6)) having carbon-carbon double bond in the molecule to asymmetric epoxidation to produce an optically active epoxy compound (formula (7), (8) or (9)). The present invention relates also to a complex used for the production method and a production method of the complex.
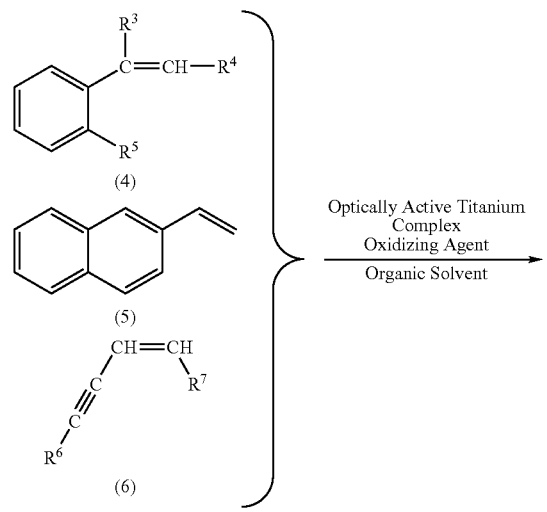
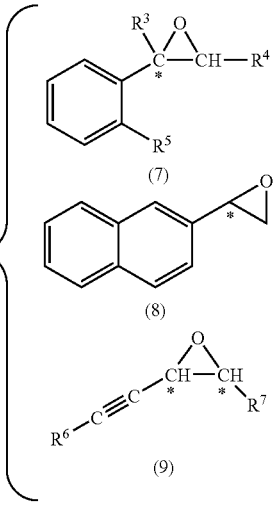
15 Claims, No Drawings

PRODUCTION METHOD OF OPTICALLY ACTIVE EPOXY COMPOUND, COMPLEX USED FOR THE METHOD AND PRODUCTION METHOD OF THE COMPLEX

BACKGROUND OF THE INVENTION

1. Field of the Art

The present invention relates to a novel optically active titanium complex and the ligand thereof, and a production method of optically active epoxy compound by use of the complex.

2. Description of the Related Art

Optically active epoxy compounds have been widely used as intermediates of several medicines represented by optically active benzopyran compounds that are effective for treating hypertension, asthma or the like, and the synthetic methods of the compounds have been widely considered. Among the synthetic methods, asymmetric epoxidation of carbon-carbon double bond is the most practical method, since asymmetric epoxidation by use of titanium tartrate as a catalyst was found (Non-patent document 1), several synthetic methods through asymmetric epoxidation have been developed (Non-patent Documents 2 and 3).

However, many of these synthetic methods are methods in which an oxidizing agent having a low atom economy, such as hypochlorite, iodobenzene or the like is used. Thus, it is strongly desired to develop any methods having a higher atom economy and further any synthetic methods by use of an environment-friendly oxidizing agent. Among several oxidizing agents, hydrogen peroxide is said to be an environment-friendly oxidizing agent as it has a high atom economy and it is transformed into water after oxidation. Therefore, asymmetric epoxidations by use of hydrogen peroxide as an oxidizing agent have been eagerly studied, but only a few examples can achieve epoxidation in a high enantioselectivity manner (Non-patent Documents 4 and 5), and in many cases there is a problem that the turnover number of catalysts is insufficient.

It is reported in 2005 that the asymmetric epoxidation of several olefins by use of hydrogen peroxide as an oxidizing agent proceeds in a high enantioselectivity manner when a di-μ-oxotitanium salalen complex is used as a catalyst. However, there is a problem in this asymmetric epoxidation that as the di-μ-oxotitanium salalen complex is a giant molecule having a molecular weight of nearly 2000, the synthesis of the complex requires a long time and a high cost. Further, there is also a problem that the method is insufficient in applicability aspect as it goes through intermolecular Meerwein-Ponndorf-Verley reduction for the synthesis of the complex (Non-patent Document 6). Thereafter, it is reported in 2006 that the asymmetric epoxidation of several olefins by use of hydrogen peroxide as an oxidizing agent proceeds in a high enantioselectivity manner when a di-μ-oxotitanium salan complex is used as a catalyst. Although this asymmetric epoxidation overcomes problems in the above-mentioned method by use of di-μ-oxotitanium salalen complex that the synthetic method of complex is difficult and it goes through a special reaction, and thus is an excellent technique, it has problems that optical yield or chemical yield is not sufficient depending on the substrates (Non-patent Document 7 and Patent Document 1).

Patent Document 1: WO 2006/087874 A1

Non-patent Document 1: T. Katsuki, K. B. Sharpless, J. Am. Chem. Soc. (1980), 102, 5974-5796

Non-patent Document 2: E. N. Jacobsen, M. H. Wu, "Comprehensive Asymmetric Catalysis" Ed. by Jacobsen, E. N.; Pfaltz, A.; Yamamoto, H. Springer (1999), Vol. II, 21, pp. 649-677

Non-patent Document 3: T. Katsuki, "Comprehensive Coordination Chemistry II" Ed. by McCleverty, J., Elsevier Science Ltd., Oxford (2003), Vol. 9, Chapter 9.4, pp. 207-264

Non-patent Document 4: L. Shu, Y Shi, Tetrahedron, (2001), 57, 5213-5218

Non-patent Document 5: S. Colonna, H. Molinari, S. Banfi, S. Julia, J. Masana, z, Tetrahedron, (1983), 39, 1635-1641

Non-patent Document 6: K. Matsumoto, Y Sawada, B. Saito, K. Sakai, T. Katasuki, Angew. Chem. Int. Ed. (2005), 44, 4935-4939

Non-patent Document 7: Y Sawada, K. Matsumoto, S. Kondo, H. Watanabe, T. Ozawa, K. Suzuki, B. Saito, K. Sakai, T. Katasuki, Angew. Chem. Int. Ed. (2006), 45, 3478-3480

DISCLOSURE OF INVENTION

Problem to be Solved by the Invention

An object of the present invention is to solve the above-mentioned problems in the prior art and to provide a production method of optically active epoxy compounds that is industrially useful, and a complex used as a catalyst in the method and a ligand of the complex.

Means for Solving the Problem

The present inventors eagerly investigated a production method of optically active epoxy compounds that is industrially useful, and a complex used as a catalyst in the method and a ligand of the complex. As a result, they identified the skeleton that is necessary for expressing a high catalyst activity of optically active titanium salan complex, and the substituent that is useful therefor and the position of the substituent, and found that optically active epoxy compounds can be produced with a high enantioselectivity and a high chemical yield compared with a case where the prior optically active titanium salan complex is used, and completed the present invention.

[1] A production method of an optically active epoxy compound of formulae (7), (8) or (9)

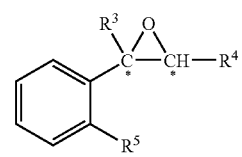

(7)

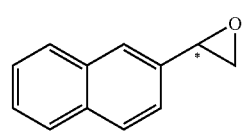

(8)

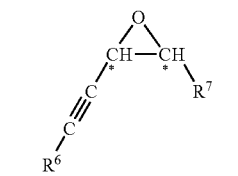

(9)

wherein $R^3$ is hydrogen atom or methyl group, $R^4$ and $R^5$ are hydrogen atom, or $R^4$ and $R^5$ together form —CH$_2$—, —CH$_2$CH$_2$—, —CH$_2$CH$_2$CH$_2$— or —CH$_2$O— (the oxygen atom in the —CH$_2$O— is bonded at $R^5$ side), $R^6$ is a phenyl group, $R^7$ is methyl group or ethyl group, the carbon atom shown with * is optically active, characterized by comprising subjecting an unsaturated compound of formula (4), (5) or (6)

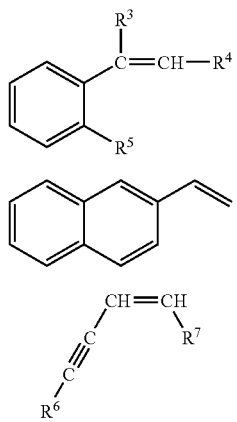

(4)

(5)

(6)

wherein $R^3$, $R^4$, $R^5$, $R^6$ and $R^7$ are as defined above, to asymmetric epoxidation with a peracid by using as a catalyst an optically active titanium complex of formula (1) or (1')

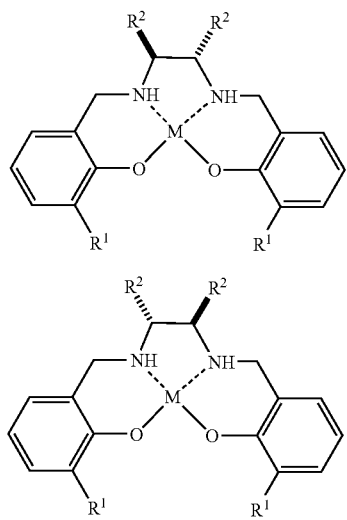

(1)

(1')

wherein $R^1$ is a phenyl group (the phenyl group is substituted with methyl group, ethyl group (the methyl group and the ethyl group are substituted with at least one halogen atom) or $C_{1-7}$alkoxy group), $R^2$ is $C_{3-5}$ divalent group in which two $R^2$s together form a ring, M is TiJ$^1$J$^2$ (in TiJ$^1$J$^2$, Ti is titanium atom, J$^1$ and J$^2$ independently of each other are a halogen atom, $C_{1-4}$alkoxy group, or J$^1$ and J$^2$ together show oxygen atom, or J$^1$ and J$^2$ together form a ring that is a divalent group of formula (2)

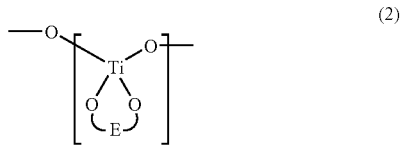

(2)

(a partial structure O-E-O in the formula is shown by formula (3) in the compound of formula (1) and by formula (3') in the compound of formula (1')

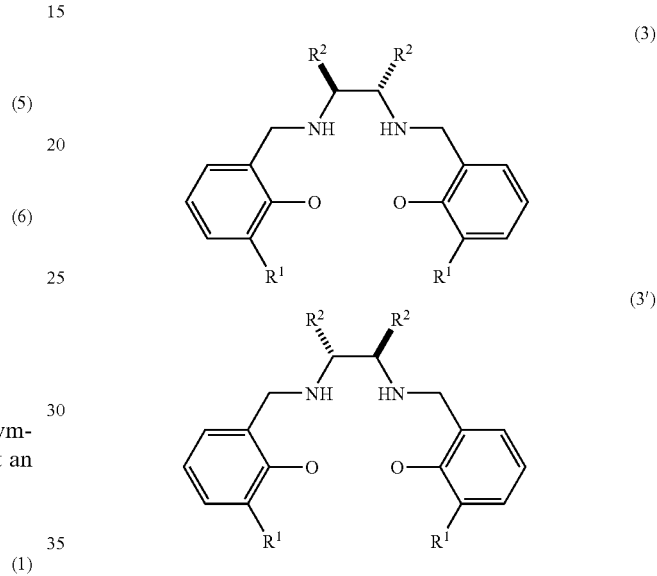

(3)

(3')

wherein $R^1$ and $R^2$ are as defined above)).

[2] The production method of an optically active epoxy compound as set forth in [1], wherein $R^2$ is tetramethylene group that two $R^2$s together form.

[3] The production method of an optically active epoxy compound as set forth in [2], wherein $R^1$ is 2-methylphenyl group (the methyl group in the 2-methylphenyl group is substituted with at least one halogen atom).

[4] The production method of an optically active epoxy compound as set forth in [3], wherein $R^1$ is 2-trifluoromethylphenyl group.

[5] The production method of an optically active epoxy compound as set forth in [2], wherein $R^1$ is 2-methoxyphenyl group.

[6] An optically active titanium complex of formula (1) or (1')

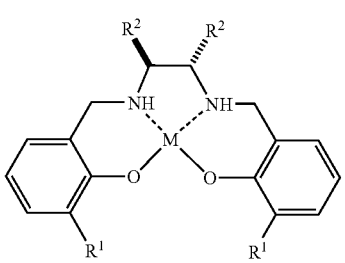

(1)

-continued (1')

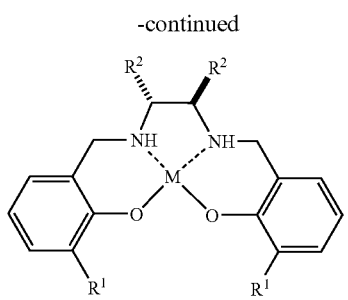

wherein R¹ is 2-trifluoromethylphenyl group or 2-methoxyphenyl group, R² is $C_{3-5}$ divalent group in which two R²s together form a ring, M is $TiJ^1J^2$ (in $TiJ^1J^2$, Ti is titanium atom, J¹ and J² independently of each other are a halogen atom, $C_{1-4}$alkoxy group, or J¹ and J² together show oxygen atom, or J¹ and J² together form a ring that is a divalent group of formula (2)

(2)

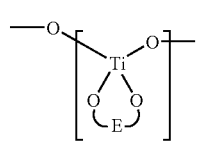

(a partial structure O-E-O in the formula is shown by formula (3) in the compound of formula (1) and by formula (3') in the compound of formula (1')

(3)

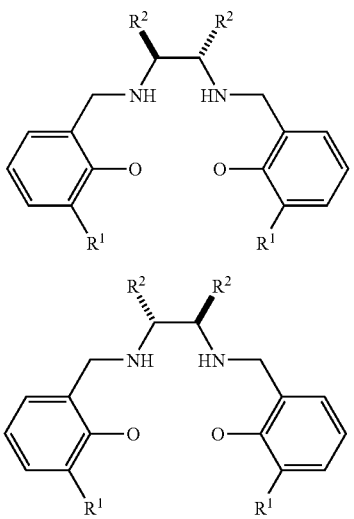

(3')

wherein R¹ and R² are as defined above)).

[7] The optically active titanium complex as set forth in [6], wherein R¹ is 2-trifluoromethylphenyl group, R² is tetramethylene group that two R²s together form.

[8] The optically active titanium complex as set forth in [6], wherein R¹ is 2-methoxyphenyl group, R² is tetramethylene group that two R²s together form.

[9] A salan ligand of formulae (10) and (10')

(10)

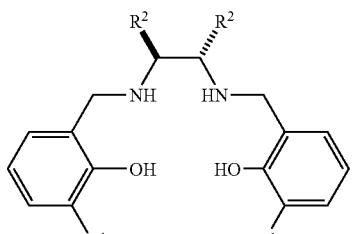

(10')

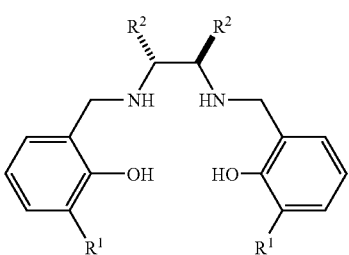

wherein R¹ is 2-trifluoromethylphenyl group, R² is tetramethylene group that two R²s together form.

[10] A salan ligand of formulae (10) and (10')

(10)

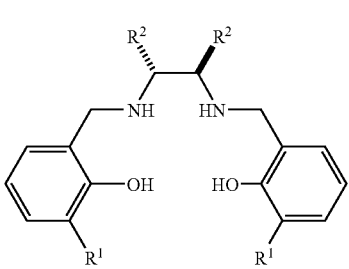

(10')

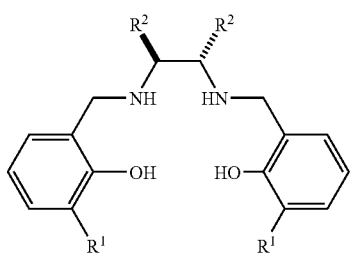

wherein R¹ is 2-methoxyphenyl group, R² is tetramethylene group that two R²s together form.

[11] The production method as set forth in any one of [1] to [5], wherein aqueous hydrogen peroxide is used as the peracid.

Effect of the Invention

According to the present invention, unsaturated compounds having prochiral carbon-carbon double bond in the molecule can be epoxidized in a high enantioselectivity, and thus optically active epoxy compounds can be produced. In addition, the complex of the present invention is very useful as a catalyst in the production method. Further, the optically active epoxy compounds obtained by the production method of the present invention are useful as optically active pharmaceutical intermediates of the compounds that are effective for treating hypertension, asthma or the like.

Best Mode for Carrying Out the Invention

In the present specification, "n" means normal, "i" means iso, "s" means secondary, "t" means tertiary, "c" means cyclo, "o" means ortho, "m" means meta, and "p" means para.

Hereinafter, the present invention is described in detail. The production method of optically active epoxy compound according to the present invention is characterized by being able to produce an optically active epoxy compound of compound of formulae (7), (8) or (9)

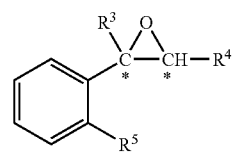
(7)

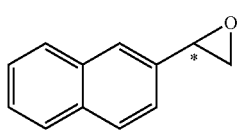
(8)

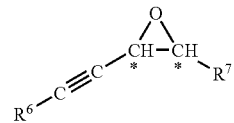
(9)

wherein $R^3$ is hydrogen atom or methyl group, $R^4$ and $R^5$ are hydrogen atom, or $R^4$ and $R^5$ together form —$CH_2$—, —$CH_2CH_2$—, —$CH_2CH_2CH_2$— or —$CH_2O$— (the oxygen atom in the —$CH_2O$— is bonded at $R^5$ side), $R^6$ is a phenyl group, $R^7$ is methyl group or ethyl group, the carbon atom shown with * is optically active, characterized by comprising subjecting an unsaturated compound of formula (4), (5) or (6)

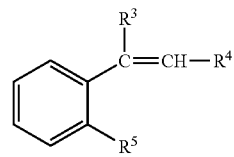
(4)

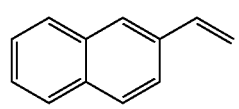
(5)

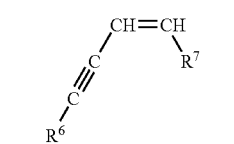
(6)

wherein $R^3$, $R^4$, $R^5$, $R^6$ and $R^7$ are as defined above, to asymmetric epoxidation with a peracid by using as a catalyst an optically active titanium complex of formula (1) or (1')

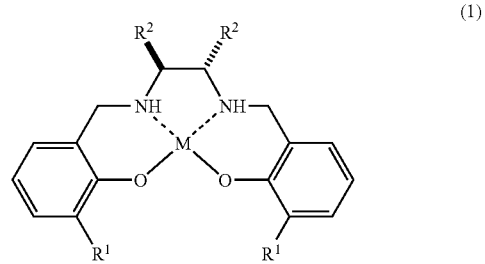
(1)

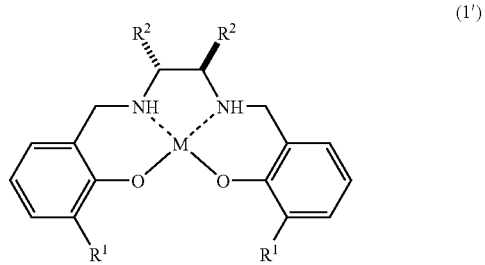
(1')

wherein $R^1$ is a phenyl group (the phenyl group is substituted with methyl group, ethyl group (the methyl group and the ethyl group are substituted with at least one halogen atom) or $C_{1-7}$alkoxy group), $R^2$ is $C_{3-5}$ divalent group in which two $R^2$s together form a ring, M is $TiJ^1J^2$ (in $TiJ^1J^2$, Ti is titanium atom, $J^1$ and $J^2$ independently of each other are a halogen atom, $C_{1-4}$alkoxy group, or $J^1$ and $J^2$ together show oxygen atom, or $J^1$ and $J^2$ together form a ring that is a divalent group of formula (2)

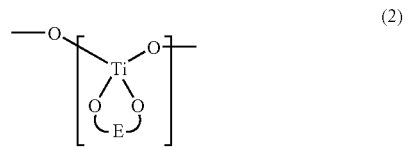
(2)

(a partial structure O-E-O in the formula is shown by formula (3) in the compound of formula (1) and by formula (3') in the compound of formula (1')

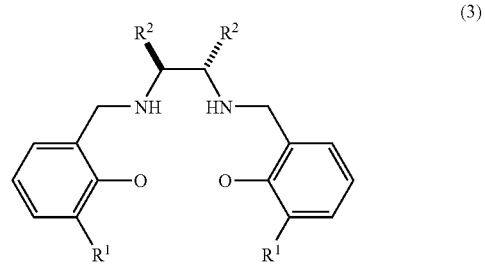
(3)

-continued

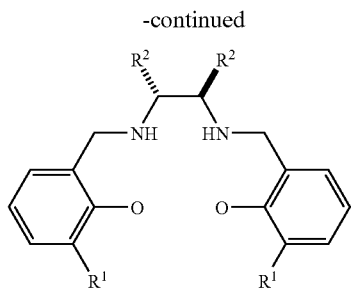
(3')

wherein $R^1$ and $R^2$ are as defined above)).

Each substituent in the formulae (1) and (1') is explained.

$R^1$ in the formulae (1) and (1') is a phenyl group (the phenyl group is substituted with methyl group, ethyl group (the methyl group and the ethyl group are substituted with at least one halogen atom) or $C_{1-7}$alkoxy group).

$R^1$ in the formulae (1) and (1') is preferably is 2-methylphenyl group (the methyl group in the 2-methylphenyl group is substituted with at least one halogen atom), 2-methoxyphenyl group, 2-ethoxyphenyl group, or 2-i-propoxyphenyl group, and more preferably 2-methoxyphenyl group, or 2-trifluoromethylphenyl group.

$R^2$ in the formulae (1) and (1') is $C_{3-5}$ divalent group in which two $R^2$s together form a ring.

$R^2$ in the formulae (1) and (1') is concretely described. $R^2$ includes trimethylene group, tetramethylene group or the like in which two $R^2$s together form a ring, and preferably $R^2$ is tetramethylene group.

$R^3$ in the formulae (1) and (1') is concretely described. $R^3$ is hydrogen atom or methyl group, and preferably hydrogen atom. In addition, when $R^4$ and $R^5$ together form a divalent group of —$CH_2CH_2$—, preferable $R^3$ includes hydrogen atom or methyl group.

$R^4$ and $R^5$ in the formulae (1) and (1') is concretely described. $R^4$ and $R^5$ are hydrogen atom or $R^4$ and $R^5$ together form a divalent group of —$CH_2$—, —$CH_2CH_2$—, —$CH_2CH_2CH_2$— or —$CH_2O$— (the oxygen atom in the —$CH_2O$— is bonded at $R^5$ side), and preferably $R^4$ and $R^5$ are hydrogen atom or $R^4$ and $R^5$ together form a divalent group of —$CH_2$—, or —$CH_2CH_2CH_2$—.

$R^7$ in the formulae (1) and (1') is concretely described. $R^7$ is methyl group or ethyl group, and more preferably methyl group.

M in the formulae (1) and (1') is $TiJ^1J^2$ (in $TiJ^1J^2$, Ti is titanium atom, $J^1$ and $J^2$ independently of each other are a halogen atom, $C_{1-4}$alkoxy group, or $J^1$ and $J^2$ together show oxygen atom, or $J^1$ and $J^2$ together form a ring that is a divalent group of formula (2)

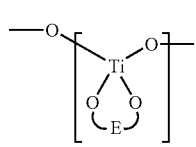
(2)

(a partial structure O-E-O in the formula is shown by formula (3) in the compound of formula (1) and by formula (3') in the compound of formula (1'))

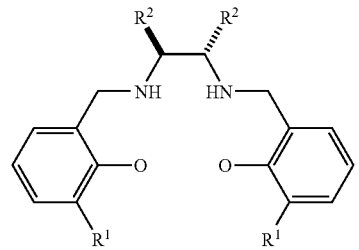
(3)

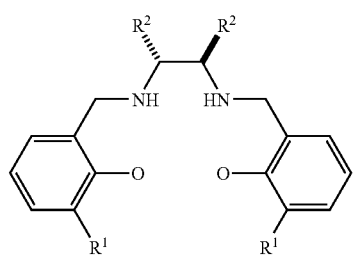
(3')

wherein $R^1$ and $R^2$ are as defined above)).

M in the formulae (1) and (1') is concretely described. It is preferable that $J^1$ and $J^2$ in M independently of each other are isopropoxy group, or $J^1$ and $J^2$ together show oxygen atom, $J^1$ and $J^2$ together form a ring that is a divalent group of formula (2)

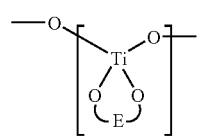
(2)

(a partial structure O-E-O in the formula is shown by formula (3) in the compound of formula (1) and by formula (3') in the compound of formula (1'))

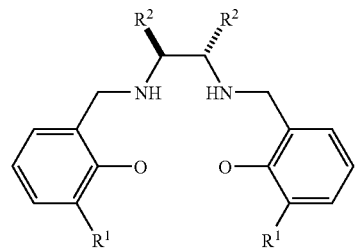
(3)

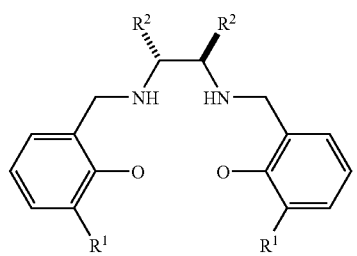
(3')

wherein $R^1$ and $R^2$ are as defined above)). It is more preferable that $J^1$ and $J^2$ together form a ring that is a divalent group of formula (2)

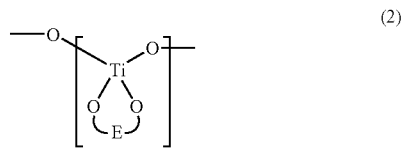

(2)

(a partial structure O-E-O in the formula is shown by formula (3) in the compound of formula (1) and by formula (3') in the compound of formula (1'))

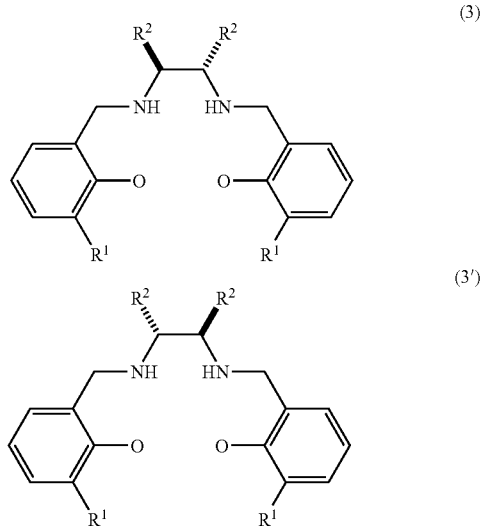

(3)

(3')

wherein $R^1$ and $R^2$ are as defined above)).

The optically active titanium complex in the present invention is μ-oxotitanium binuclear complex being a divalent group of formula (2) that $J^1$ and $J^2$ together form a ring. In addition, it is assumed that the above-mentioned μ-oxotitanium binuclear complex in the production method of the present invention is formed by reacting a salen ligand with titanium alkoxide to form a titanium complex in which $J^1$ and $J^2$ independently of each other are $C_{1-4}$alkoxy group, and then forming μ-oxotitanium binuclear complex through a mononuclear oxotitanium complex in which $J^1$ and $J^2$ together show oxygen atom. Therefore, the optically active titanium complex in the present invention may be a mixture of these complexes in three states. Further, the optically active titanium complex in the present invention can be in a state of μ-oxotitanium b-nuclear complex wherein b is an integer of 3 to 10.

The optically active titanium complex of formulae (1) and (1') can be produced according to the methods described in Patent Document 1 and Non-patent Document 7. That is, a titanium compound is reacted with the salan ligand of formula (10) or (10'), then treated with water or water-containing solvent (the water-containing solvent is a mixed solvent containing water in an amount of 0.1 to 100% by mass in an organic solvent, and THF, methanol and i-propanol, etc. are used as the organic solvent). Further, water addition can be performed also by adding aqueous hydrogen peroxide.

The used titanium compounds include titanium tetrachloride, or titanium tetrabromide, the titanium alkoxides include titanium tetramethoxide, titanium tetraethoxide, titanium tetra n-propoxide, titanium tetra i-propoxide, titanium tetra n-butoxide, titanium tetra t-butoxide or the like. Among the titanium compounds, titanium tetra i-propoxide [Ti(Oi-Pr)$_4$] is preferable. Further, the used amount of the titanium compound is preferably a range from 1 to 2 mol, more preferably a range from 1 to 1.2 mol based on 1 mol of the salan ligand. In addition, the used amount of water is preferably a range from 1 to 1000 mol, more preferably a range from 1 to 10 mol based on 1 equivalent of the salan ligand. In the meantime, the production method of optically active epoxy compound according to the present invention can be also performed by forming the above-mentioned optically active titanium salan complex in the reaction system and subjecting a compound having prochiral carbon-carbon double bond in the molecule to asymmetric epoxidation without isolation of the catalyst.

The reaction solvents used in the production of the optically active titanium salan complex of formulae (1) and (1') are aprotic organic solvents, protic organic solvents or mixtures of these solvents. The aprotic organic solvents include halogen-based solvents, aromatic hydrocarbon-based solvents, ester-based solvents, ether-based solvents, amide-based solvents or nitrile-based solvents, and are concretely dichloromethane, chloroform, 1,2-dichloroethane, toluene, ethyl acetate, tetrahydrofuran, diethyl ether, dimethylformamide (DMF), butyronitrile, propionitrile, acetonitrile and the like. The protic organic solvents include alcohol-based solvents, and are ethanol, i-propanol or t-butanol, etc. Preferable reaction solvents are dichloromethane 1,2-dichloroethane and toluene that are aprotic solvents. Further preferable solvent is dichloromethane.

The salen ligands of the formulae (10) and (10') can be produced by reducing the salen ligand of formula (11) or (11')

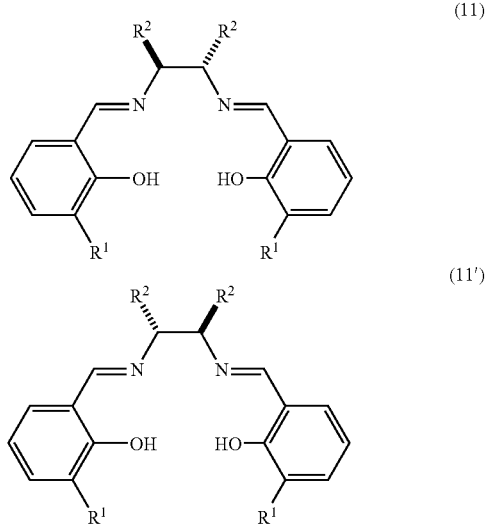

(11)

(11')

wherein $R^1$ and $R^2$ are as defined above. Reducing agents used in the reduction are preferably sodium borohydride (NaBH$_4$), sodium cyanotrihydridoborate (NaBH$_3$CN) and lithium aluminum hydride (LiAlH$_4$), etc. Sodium borohydride (NaBH$_4$) is preferable.

The structure of the salan ligands of particularly preferable optically active titanium salan complexes having a combination of the above-mentioned preferable substituents is as follows. In the structure of the salan ligand of formulae (10) and (10'), $R^1$ is preferably 2-methoxyphenyl group or 2-trifluoromethylphenyl group, and $R^2$ is preferably tetramethylene group that is a divalent group that $R^2$s together form a ring, and the salan ligand of formula (12), (12'), (13) or (13')

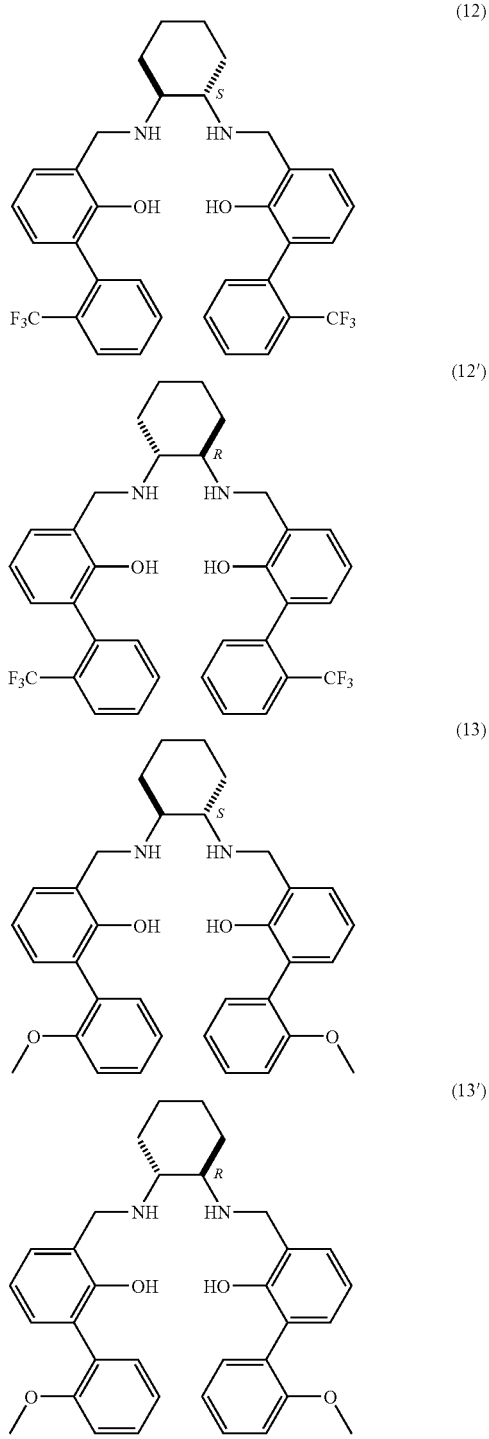

is particularly preferable.

The starting materials for the production method of optically active epoxy compound according to the present invention are the unsaturated compounds of formulae (4), (5) and (6) that are compounds having prochiral carbon-carbon double bond in the molecule. In the meantime, the epoxy compounds produced according to the method of the present invention have the structure of the formulae (7), (8) and (9) in which the carbon-carbon double bond of the starting material is transformed into an epoxy bond. For example, in a case where the compound of formula (4) is used as a starting material, the resulting optically active epoxy compound is shown by the formula (7), in a case where the compound of formula (5) is used as a starting material, the resulting optically active epoxy compound is shown by the formula (8), and in a case where the compound of formula (6) is used as a starting material, the resulting optically active epoxy compound is shown by the formula (9).

The production method of the present invention can provide only either of enantiomers in a high selectivity. In addition, the production method of the present invention can provide selectively both enantiomers of optically active epoxy compounds by using either the complex of formula (1) or the complex of formula (1').

$R^4$ and $R^5$ in the formula (4) may together form a divalent group. When $R^4$ and $R^5$ together form —$CH_2O$— (the oxygen atom in the —$CH_2O$— is bonded at $R^5$ side), a 6-membered ring is formed, and the compounds include benzopyran and the derivatives thereof. In addition, when $R^4$ and $R^5$ together form —$CH_2$—, a 5-membered ring is formed, the compounds include indene and the derivatives thereof. Further, when $R^4$ and $R^5$ together form —$CH_2CH_2$—, a 6-membered ring is formed, the compounds include 1,2-dihydronaphthalene and the derivatives thereof. Still further, when $R^4$ and $R^5$ together form —$CH_2CH_2CH_2$—, a 7-membered ring is formed, the compounds include 1,2-benzo-1,3-cycloheptadiene and the derivatives thereof.

The peracid used in the method of the present invention is preferably aqueous hydrogen peroxide and urea-hydrogen peroxide addition compound (UHP), and aqueous hydrogen peroxide is more preferable. The concentration of aqueous hydrogen peroxide is not specifically limited but from the viewpoint of industrial aspect and availability, it is preferable to use a product having a concentration of about 30% that is commercially available. In addition, aqueous hydrogen peroxide may be added dropwise in limited amounts to an epoxidation reaction solution. In this case, the used amount of the catalyst can be reduced. In the meantime, the used amount of the oxidizing agent is preferably a range from 1 to 10 equivalents (eq), more preferably a range from 1 to 1.2 equivalents (eq) based on an unsaturated compound being a substrate. The used amount of the catalyst is preferably a range from 0.01 to 100 mol %, more preferably a range from 0.01 to 10 mol % based on an unsaturated compound being a substrate.

The production method of optically active epoxy compound according to the present invention is generally performed in an organic solvent. The organic solvent are preferably aprotic organic solvents, and concretely include hydrocarbon halogenides such as dichloromethane ($CH_2Cl_2$), 1,2-dichloroethane (1,2-$CH_2ClCH_2Cl$), chlorobenzene or the like, aromatic hydrocarbons such as toluene or the like, esters such as ethyl acetate or the like, ethers such as tetrahydrofuran (THF) or the like. Preferable solvents are hydrocarbon halogenides, and more preferable solvent is dichloromethane. Further, when aqueous hydrogen peroxide is used as an oxidizing agent, the reaction solution may be two-phase system composed of an organic phase and an aqueous phase.

The reaction temperature of the production method of optically active epoxy compound according to the present invention is not specifically limited, but it is preferable to perform the method at 0 to 50° C., and it is more preferable to perform the method at 20 to 30° C. Further, reaction time is not specifically limited, and suitably selected depending on the reaction temperature.

EXAMPLES

Hereinafter, the present invention will be described in further detail based on examples to which the present invention is not limited.

(Method A)

The preparation of a catalyst in the reaction system and the production method of optically active epoxy compound (Method A) are as follows. The salen ligand of formula (14')

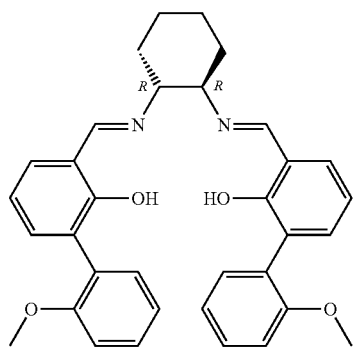

(14')

wherein R means (R) of absolute configuration, was reduced with NaBH$_4$ to synthesize the salan ligand of formula (13')

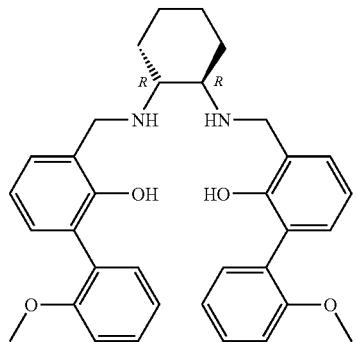

(13')

wherein R means (R) of absolute configuration. In a dichloromethane solution (0.5 mL) in which the salan ligand of formula (13') (3.2 mg, 0.006 mmol) was dissolved, a dichloromethane solution in which Ti(Oi-Pr)$_4$ (1.4 mg, 0.005 mmol) was dissolved was added and stirred at 25° C. for 1 hour. Thereafter, continuously without isolation of the optically active titanium salan complex, an unsaturated compound having carbon-carbon double bond (0.10 mmol), and then commercially available 30% aqueous hydrogen peroxide (0.11 mmol) were added, and stirred at a reaction temperature of 25° C. for 9 hours. The solvent of the reaction mixture was distilled off under reduced pressure, and purification procedure with silica gel chromatography was performed to obtain an aimed optically active epoxy compound. In addition, the optical purity of the resulting optically active epoxy compound was analyzed with an optically active high performance liquid chromatography column. Further, the analysis of the optically active titanium salan complex was carried out with ESI-MS manufactured by JEOL Ltd., and m/z was 1201.46 (theoretical value: 1201.43). Substrates 1 to 6 of the following formulae

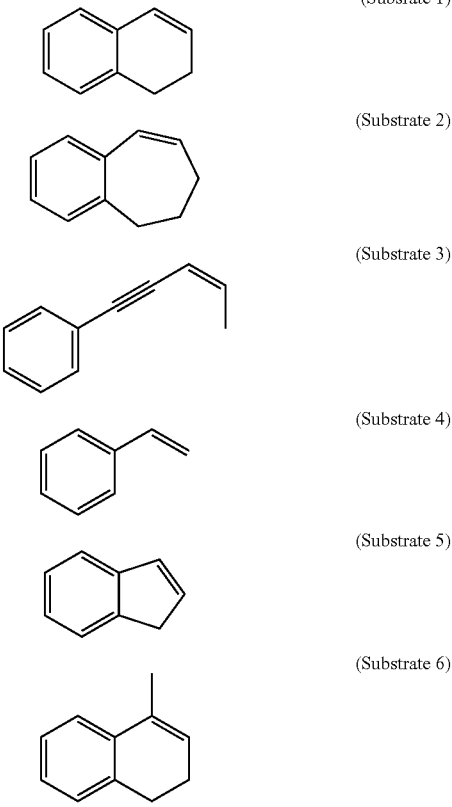

were subjected to asymmetric epoxidation as unsaturated compounds having carbon-carbon double bond according to the above-mentioned Method A, and thereby as optically active epoxy compounds, Products 1 to 6 of the following formulae

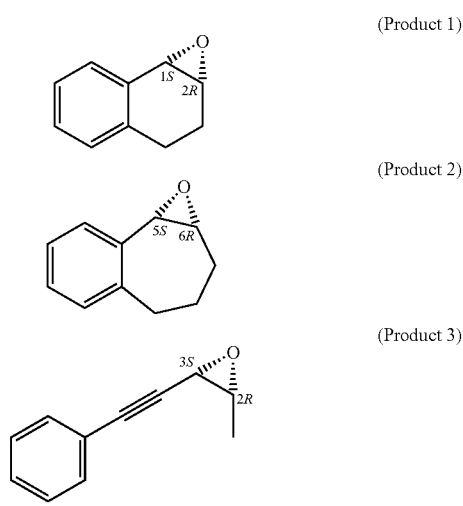

(Product 4)

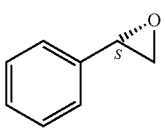

(Product 5)

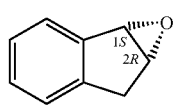

(Product 6)

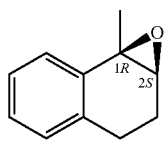

were obtained from Substrates 1 to 6, respectively. In the meantime, the yield of the products was analyzed with $^1$H-NMR (400 MHz). The enantiomer excess rate of Product 1 was analyzed by use of Daicel Chiralcell OB-H and hexan/isopropanol (99/1=v/v) mixed liquid, the enantiomer excess rate of Product 2 was analyzed by use of Daicel Chiralpack AS-H and hexan/isopropanol (999/1=v/v) mixed liquid, the enantiomer excess rate of Product 3 was analyzed by use of Daicel Chiralcell OD-H and hexan/isopropanol (99/1=v/v) mixed liquid, the enantiomer excess rate of Product 4 was analyzed by use of Daicel Chiralcell OD-H and hexan/isopropanol (999/1=v/v) mixed liquid, the enantiomer excess rate of Product 5 was analyzed by use of Daicel Chiralcell OB-H and hexan/isopropanol (9/1=v/v) mixed liquid, and the enantiomer excess rate of Product 6 was analyzed by use of Daicel Chiralcell OB-H and hexan/isopropanol (99/1=v/v) mixed liquid, in which a high performance liquid chromatography (HPLC) was used.

Examples 1 to 7

Examples in which a catalyst was prepared from the salan ligand of formula (13') and Ti(Oi-Pr)$_4$ in situ and an optically active epoxy compound was produced, are shown in Table 1. In Example 5, the used amount of the salan ligand and Ti(Oi-Pr)$_4$ was altered, and the reaction was carried out similarly to Method A. In Examples 6 and 7, the reaction time was altered to 6 hours, and the reaction was carried out similarly to Method A.

TABLE 1

| | | Catalyst (prepared in situ) | | | | | | | Enantiomer Excess Rate |
|---|---|---|---|---|---|---|---|---|---|
| | Substrate*2 (unsaturated compound) | Salan Ligand (mol %)*1 | Ti(Oi-Pr)$_4$ (mol %)*1 | Oxidizing Agent | Solvent | Reaction Time (hour) | Product*2 (epoxy compound) | Yield (%) | (% ee, absolute configuration) |
| Example 1 | Substrate 1 | 6 | 5 | Aqueous hydrogen peroxide | Dichloromethane | 9 | Product 1 | 89 | 98, (1S, 2R) |
| Example 2 | Substrate 2 | 6 | 5 | Aqueous hydrogen peroxide | Dichloromethane | 9 | Product 2 | 66 | 97, (5S, 6R) |
| Example 3 | Substrate 3 | 6 | 5 | Aqueous hydrogen peroxide | Dichloromethane | 9 | Product 3 | 84 | 94, (2R, 3S) |
| Example 4 | Substrate 4 | 6 | 5 | Aqueous hydrogen peroxide | Dichloromethane | 9 | Product 4 | 68 | 89, (S) |
| Example 5 | Substrate 4 | 5 | 4 | Aqueous hydrogen peroxide | Dichloromethane | 9 | Product 4 | 62 | 89, (S) |
| Example 6 | Substrate 5 | 6 | 5 | Aqueous hydrogen peroxide | Dichloromethane | 6 | Product 5 | 86 | 98, (1S, 2R) |
| Example 7 | Substrate 6 | 6 | 5 | Aqueous hydrogen peroxide | Dichloromethane | 6 | Product 6 | 81 | 96, (1R, 2S) |

*1 The used amount of salan ligand (13') and Ti(Oi-Pr)$_4$ based on the substrate.
*2 The structure of the substrate and the product is shown above.

(Method B)

The preparation of a catalyst in situ and the production method of optically active epoxy compound (Method B) are as follows. In a dichloromethane solution (0.5 mL) in which the salan ligand (3.7 mg, 0.006 mmol) of formula (12')

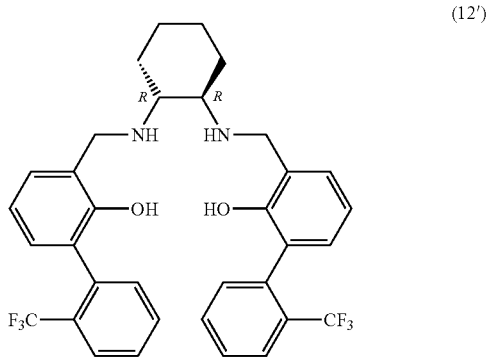

(12')

wherein R means (R) of absolute configuration, was dissolved, a dichloromethane solution in which Ti(Oi-Pr)$_4$ (1.4 mg, 0.005 mmol) was dissolved was added and stirred at 25° C. for 1 hour. Thereafter, continuously without isolation of the optically active titanium salan complex, an unsaturated compound having carbon-carbon double bond (0.10 mmol), and then commercially available 30% aqueous hydrogen peroxide (0.11 mmol) were added, and stirred at a reaction temperature of 25° C. for 9 hours. The solvent of the reaction mixture was distilled off under reduced pressure, and purification procedure with silica gel chromatography was performed to obtain an aimed optically active epoxy compound.

Examples 8 to 14

Examples in which a catalyst was prepared from the salan ligand of formula (12') and Ti(Oi-Pr)$_4$ in situ and an optically active epoxy compound was produced, are shown in Table 2. In Example 12, the used amount of the salan ligand and Ti(Oi-Pr)$_4$ was altered, and the reaction was carried out similarly to Method B. In Examples 13 and 14, the reaction time was altered to 6 hours, and the reaction was carried out similarly to Method B.

TABLE 2

| | | Catalyst (prepared in situ) | | | | | | | Enantiomer Excess Rate |
|---|---|---|---|---|---|---|---|---|---|
| | Substrate*2 (unsaturated compound) | Salan Ligand (mol %)*1 | Ti(Oi-Pr)$_4$ (mol %)*1 | Oxidizing Agent | Solvent | Reaction Time (hour) | Product*2 (epoxy compound) | Yield (%) | (% ee, absolute configuration) |
| Example 8 | Substrate 1 | 6 | 5 | Aqueous hydrogen peroxide | Dichloromethane | 9 | Product 1 | 93 | 98, (1S, 2R) |
| Example 9 | Substrate 2 | 6 | 5 | Aqueous hydrogen peroxide | Dichloromethane | 9 | Product 2 | 78 | 98, (5S, 6R) |
| Example 10 | Substrate 3 | 6 | 5 | Aqueous hydrogen peroxide | Dichloromethane | 9 | Product 3 | 92 | 96, (2R, 3S) |
| Example 11 | Substrate 4 | 6 | 5 | Aqueous hydrogen peroxide | Dichloromethane | 9 | Product 4 | 80 | 87, (S) |
| Example 12 | Substrate 4 | 5 | 4 | Aqueous hydrogen peroxide | Dichloromethane | 9 | Product 4 | 71 | 87, (S) |
| Example 13 | Substrate 5 | 6 | 5 | Aqueous hydrogen peroxide | Dichloromethane | 6 | Product 5 | 77 | 98, (1S, 2R) |
| Example 14 | Substrate 6 | 6 | 5 | Aqueous hydrogen peroxide | Dichloromethane | 6 | Product 6 | 71 | 93, (1R, 2S) |

*1 The used amount of salan ligand (12') and Ti(Oi-Pr)$_4$ based on the substrate.

*2 The structure of the substrate and the product is shown above.

(Method C)

The production method of optically active epoxy compound (Method C) is as follows. The salan ligand (4.8 mg, 0.010 mmol) of formula (15')

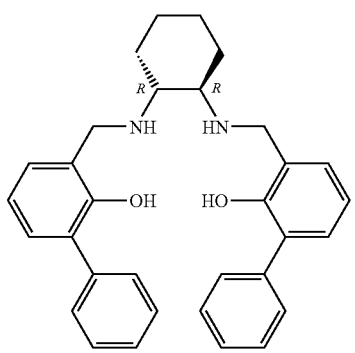

(15')

wherein R means (R) of absolute configuration, was added in a dichloromethane solution (1.0 mL, 10 mM) in which Ti(Oi-Pr)$_4$ was dissolved and stirred at 25° C. Half an hour (30 minutes) later, a drop of water was added, and further stirred for 30 minutes. Then, Substrate 1 (0.10 mmol) and 30% aqueous hydrogen peroxide (0.12 mmol) were added, and reacted by stirring at 25° C. for 6 hours. Thereafter, the solvent was distilled off under reduced pressure, and the resulting residue was purified with silica gel chromatography by use of pentane/diethyl ether (40/1=v/v) mixed liquid to obtain Product 1.

(Method D)

The production method of optically active epoxy compound (Method D) by use of an isolated catalyst is as follows. In dichloromethane (1.0 mL), the optically active titanium salan complex (5.4 mg, 0.005 mmol) of formula (16')

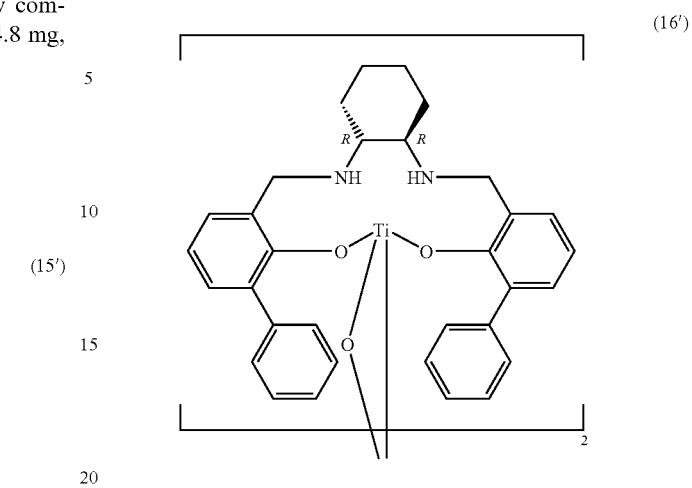

(16')

wherein R means (R) of absolute configuration and an unsaturated compound having carbon-carbon double bond (0.10 mmol) were dissolved. In the resulting reaction solution, 30% aqueous hydrogen peroxide (0.15 mmol) was added, and reacted by stirring at 25° C. for 24 hours. Thereafter, the solvent was distilled off under reduced pressure, and the resulting residue was purified with silica gel chromatography to obtain an aimed optically active epoxy compound.

Comparative Examples 1 to 8

Comparative Examples 1, 2 and 4 to 8 in which a catalyst was prepared from the salan ligand of formula (15') and Ti(Oi-Pr)$_4$ in situ and an optically active epoxy compound was produced, and Comparative Example 3 in which an optically active epoxy compound was produced by use of the isolated catalyst of formula (16') being an optically active titanium salan complex, are shown in Table 3. In Comparative Example 1, the reaction time was altered to 6 hours and the used amount of 30% aqueous hydrogen peroxide was altered to 0.12 mmol, and the reaction was carried out similarly to Method D. In Comparative Example 2, the reaction temperature was altered to 0° C. and the used amount of 30% aqueous hydrogen peroxide was altered to 0.12 mmol, and the reaction was carried out similarly to Method D.

TABLE 3

| | | Catalyst (prepared in situ) | | Isolated Catalyst Titanium | Used Amount of Aqueous | | Reaction | | | | Enantiomer Excess Rate |
|---|---|---|---|---|---|---|---|---|---|---|---|
| | Substrate*2 (unsaturated compound) | Salan Ligand (mol %)*1 | Ti(Oi-Pr)$_4$ (mol %)*1 | Salan Complex (mol %)*1 | Hydrogen Peroxide (mmol) | Solvent | Reaction Time (hour) | Temperature (° C.) | Product*2 (epoxy compound) | Yield (%) | (% ee, absolute configuration) |
| Comparative Example 1 | Substrate 1 | — | — | 5 | 0.12 | Dichloromethane | 6 | 25 | Product 1 | 87 | 96, (1S, 2R) |
| Comparative Example 2 | Substrate 1 | — | — | 5 | 0.12 | Dichloromethane | 24 | 0 | Product 1 | 79 | 96, (1S, 2R) |
| Comparative Example 3 | Substrate 1 | 10 | 10 | — | 0.12 | Dichloromethane | 6 | 25 | Product 1 | 90 | 95, (1S, 2R) |

TABLE 3-continued

| | Substrate*2 (unsaturated compound) | Catalyst (prepared in situ) | | Isolated Catalyst Titanium Salan Complex (mol %)*1 | Used Amount of Aqueous Hydrogen Peroxide (mmol) | Solvent | Reaction | | Product*2 (epoxy compound) | Yield (%) | Enantiomer Excess Rate (% ee, absolute configuration) |
| --- | --- | --- | --- | --- | --- | --- | --- | --- | --- | --- | --- |
| | | Salan Ligand (mol %)*1 | Ti(Oi-Pr)$_4$ (mol %)*1 | | | | Reaction Time (hour) | Temperature (° C.) | | | |
| Comparative Example 4 | Substrate 2 | — | — | 5 | 0.15 | Dichloromethane | 24 | 25 | Product 2 | 44 | 97, (5S, 6R) |
| Comparative Example 5 | Substrate 3 | — | — | 5 | 0.15 | Dichloromethane | 24 | 25 | Product 3 | 69 | 90, (2R, 3S) |
| Comparative Example 6 | Substrate 4 | — | — | 5 | 0.15 | Dichloromethane | 24 | 25 | Product 4 | 47 | 82, (S) |
| Comparative Example 7 | Substrate 5 | — | — | 5 | 0.15 | Dichloromethane | 24 | 25 | Product 5 | 72 | 95, (1S, 2R) |
| Comparative Example 8 | Substrate 6 | — | — | 5 | 0.15 | Dichloromethane | 24 | 25 | Product 6 | 55 | 95, (1R, 2S) |

*1The used amount of salan ligand (15'), Ti(Oi-Pr)$_4$ and titanium salan complex (16') based on the substrate.
*2The structure of the substrate and the product is shown above.

Examples 15 to 18

By use of Substrate 7 or 8 of the following formula

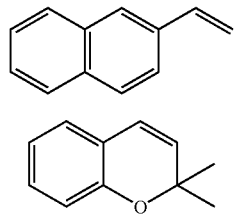

(Substrate 7)

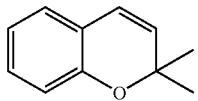

(Substrate 8)

as an unsaturated compound having carbon-carbon double bond, asymmetric epoxidation was performed according to Method A or Method B to obtain as an optically active epoxy compound, Product 7 (from Substrate 7) or Product 8 (from Substrate 8) of the following formula

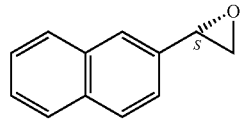

(Product 7)

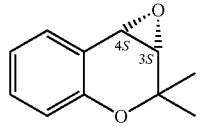

(Product 8)

The yield of the products was analyzed with $^1$H-NMR (400 MHz). The enantiomer excess rate of Product 7 was analyzed by use of Daicel Chiralcell OJ-H, and the enantiomer excess rate of Product 8 was analyzed by use of Daicel Chiralcell OB-H, in which a high performance liquid chromatography (HPLC) was used.

Examples 15 and 16

Examples in which according to Method A, a catalyst was prepared from the salan ligand of formula (13') and Ti(Oi-Pr)$_4$ in situ and an optically active epoxy compound was produced, are shown in Table 4.

TABLE 4

| | Substrate*2 (unsaturated compound) | Catalyst (prepared in situ) | | Oxidizing Agent | Solvent | Reaction Time (hour) | Product*2 (epoxy compound) | Yield (%) | Enantiomer Excess Rate (% ee, absolute configuration) |
| --- | --- | --- | --- | --- | --- | --- | --- | --- | --- |
| | | Salan Ligand (mol %)*1 | Ti(Oi-Pr)$_4$ (mol %)*1 | | | | | | |
| Example 15 | Substrate 7 | 6 | 5 | Aqueous hydrogen peroxide | Dichloromethane | 9 | Product 7 | 82 | 98, (S) |

TABLE 4-continued

| | Substrate*2 (unsaturated compound) | Catalyst (prepared in situ) | | | | Reaction Time (hour) | Product*2 (epoxy compound) | Yield (%) | Enantiomer Excess Rate (% ee, absolute configuration) |
| | | Salan Ligand (mol %)*1 | Ti(Oi-Pr)₄ (mol %)*1 | Oxidizing Agent | Solvent | | | | |
|---|---|---|---|---|---|---|---|---|---|
| Example 16 | Substrate 8 | 6 | 5 | Aqueous hydrogen peroxide | Dichloromethane | 9 | Product 8 | 75 | >99, (3S, 4S) |

*1 The used amount of salan ligand (13') and Ti(Oi-Pr)₄ based on the substrate.
*2 The structure of the substrate and the product is shown above.

Examples 17 and 18

Examples in which according to Method B, a catalyst was prepared from the salan ligand of formula (12') and Ti(Oi-Pr)₄ in situ and an optically active epoxy compound was produced, are shown in Table 5.

TABLE 5

| | Substrate*2 (unsaturated compound) | Catalyst (prepared in situ) | | | | Reaction Time (hour) | Product*2 (epoxy compound) | Yield (%) | Enantiomer Excess Rate (% ee, absolute configuration) |
| | | Salan Ligand (mol %)*1 | Ti(Oi-Pr)₄ (mol %)*1 | Oxidizing Agent | Solvent | | | | |
|---|---|---|---|---|---|---|---|---|---|
| Example 17 | Substrate 7 | 6 | 5 | Aqueous hydrogen peroxide | Dichloromethane | 9 | Product 7 | 83 | 98, (S) |
| Example 18 | Substrate 8 | 6 | 5 | Aqueous hydrogen peroxide | Dichloromethane | 9 | Product 8 | 44 | >99, (3S, 4S) |

*1 The used amount of salan ligand (12') and Ti(Oi-Pr)₄ based on the substrate.
*2 The structure of the substrate and the product is shown above.

INDUSTRIAL APPLICABILITY

The production method of the present invention can epoxidize a prochiral unsaturated compound having carbon-carbon double bond in the molecule in a high enantioselectivity to produce an optically active epoxy compound. In addition, the complex of the present invention is very useful as a catalyst in the production method. Further, the optically active epoxy compound obtained according to the production method of the present invention is useful as optically active pharmaceutical intermediates of the compounds that are effective for treating hypertension, asthma or the like.

What is claimed is:

1. A production method of an optically active epoxy compound of formulae (7), (8) or (9)

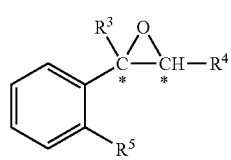
(7)

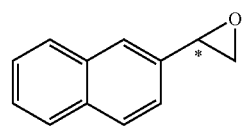
(8)

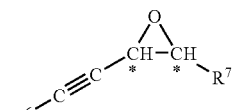
(9)

wherein $R^3$ is hydrogen atom or methyl group, $R^4$ and $R^5$ are hydrogen atom, or $R^4$ and $R^5$ together form —CH$_2$—, —CH$_2$CH$_2$—, —CH$_2$CH$_2$CH$_2$— or —CH$_2$O— (the oxygen atom in the —CH$_2$O— is bonded at $R^5$ side), $R^6$ is a phenyl group, $R^7$ is methyl group or ethyl group, the carbon atom shown with * is optically active, characterized by comprising subjecting an unsaturated compound of formula (4), (5) or (6)

(4)

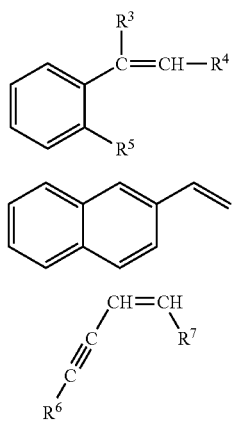

(5)

(6)

wherein $R^3$, $R^4$, $R^5$, $R^6$ and $R^7$ are as defined above, to asymmetric epoxidation with a peracid by using as a catalyst an optically active titanium complex of formula (1) or (1')

(1)

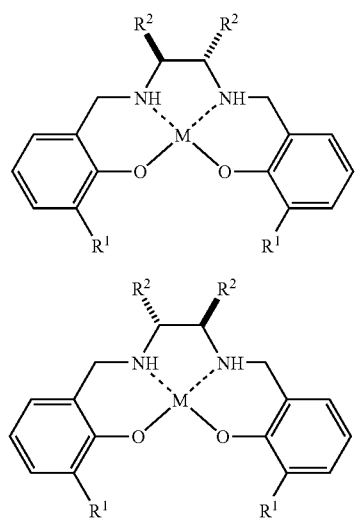

(1')

wherein $R^1$ is a phenyl group (the phenyl group is substituted with methyl group, ethyl group (the methyl group and the ethyl group are substituted with at least one halogen atom) or $C_{1-7}$alkoxy group), $R^2$ is $C_{3-5}$divalent group in which two $R^2$s together form a ring, M is $TiJ^1J^2$ (in $TiJ^1J^2$, Ti is titanium atom, $J^1$ and $J^2$ independently of each other are a halogen atom or $C_{1-4}$alkoxy group, $J^1J^2$ represents an oxygen atom, or $J^1$ and $J^2$ together form a ring that is a divalent group of formula (2)

(2)

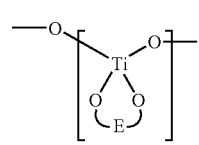

(a partial structure O-E-O in the formula is shown by formula (3) in the compound of formula (1) and by formula (3') in the compound of formula (1')

(3)

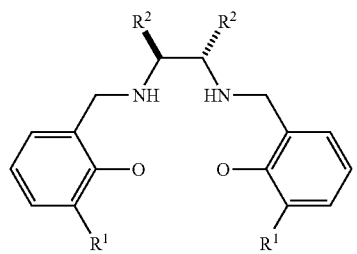

(3')

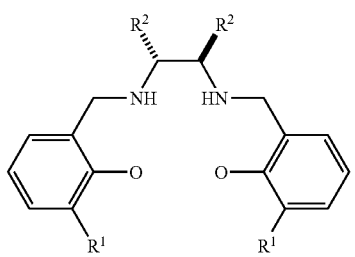

wherein $R^1$ and $R^2$ are as defined above)).

2. The production method of an optically active epoxy compound according to claim 1, wherein $R^2$ is tetramethylene group that two $R^2$s together form.

3. The production method of an optically active epoxy compound according to claim 2, wherein $R^1$ is 2-methylphenyl group (the methyl group in the 2-methylphenyl group is substituted with at least one halogen atom).

4. The production method of an optically active epoxy compound according to claim 3, wherein $R^1$ is 2-trifluoromethylphenyl group.

5. The production method of an optically active epoxy compound according to claim 2, wherein $R^1$ is 2-methoxyphenyl group.

6. An optically active titanium complex of formula (1) or (1')

(1)

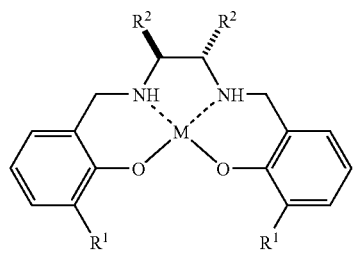

(1')

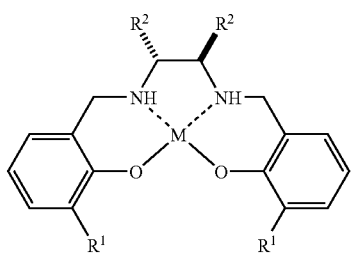

wherein $R^1$ is 2-trifluoromethylphenyl group or 2-methoxyphenyl group, $R^2$ is $C_{3-5}$ divalent group in which two $R^2$s together form a ring, M is $TiJ^1J^2$ (in $TiJ^1J^2$, Ti is titanium atom, $J^1$ and $J^2$ independently of each other are a halogen atom or $C_{1-4}$ alkoxy group, $J^1J^2$ represents an oxygen atom, or $J^1$ and $J^2$ together form a ring that is a divalent group of formula (2)

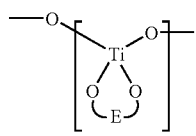
(2)

(a partial structure O-E-O in the formula is shown by formula (3) in the compound of formula (1) and by formula (3') in the compound of formula (1')

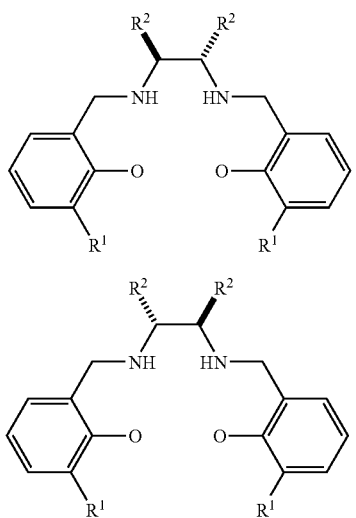
(3)

(3')

wherein $R^1$ and $R^2$ are as defined above)).

7. The optically active titanium complex according to claim 6, wherein $R^1$ is 2-trifluoromethylphenyl group, $R^2$ is tetramethylene group that two $R^2$s together form.

8. The optically active titanium complex according to claim 6, wherein $R^1$ is 2-methoxyphenyl group, $R^2$ is tetramethylene group that two $R^2$s together form.

9. A salan ligand of formulae (10) and (10')

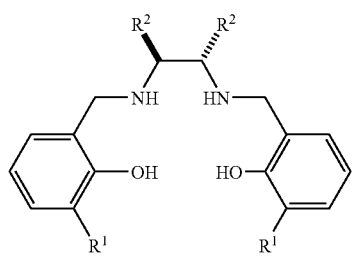
(10)

-continued

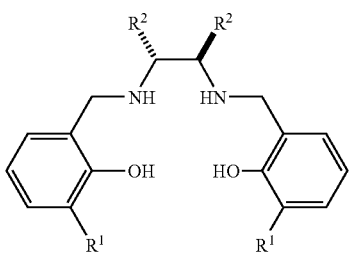
(10')

wherein $R^1$ is 2-trifluoromethylphenyl group, $R^2$ is tetramethylene group that two $R^2$s together form.

10. A salan ligand of formulae (10) and (10')

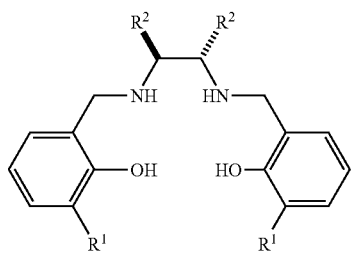
(10)

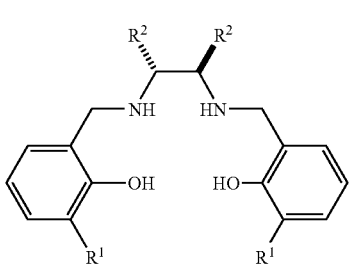
(10')

wherein $R^1$ is 2-methoxyphenyl group, $R^2$ is tetramethylene group that two $R^2$s together form.

11. The production method according to claim 1, wherein aqueous hydrogen peroxide is used as the peracid.

12. The production method according to claim 2, wherein aqueous hydrogen peroxide is used as the peracid.

13. The production method according to claim 3, wherein aqueous hydrogen peroxide is used as the peracid.

14. The production method according to claim 4, wherein aqueous hydrogen peroxide is used as the peracid.

15. The production method according to claim 5, wherein aqueous hydrogen peroxide is used as the peracid.

* * * * *